United States Patent
Ebinuma et al.

US007198905B2

(10) Patent No.: US 7,198,905 B2
(45) Date of Patent: Apr. 3, 2007

(54) METHOD OF SCREENING METHODS PREDIABETIC STATE AND SCREENING REAGENT

(75) Inventors: Hiroyuki Ebinuma, Ryugasaki (JP); Kazunori Saito, Ryugasaki (JP); Hirohito Sone, 203-102, Namiki 2-chome, Tsukuba-shi, Ibaraki (JP) 305-0044; Nobuhiro Yamada, 33-9, Ogikubo 1-chome, Suginami-ku, Tokyo (JP) 167-0051

(73) Assignees: Daiichi Pure Chemicals Co., Ltd., Tokyo (JP); Hirohito Sone, Tsukuba (JP); Nobuhiro Yamada, Tokyo (JP)

( * ) Notice: Subject to any disclaimer, the term of this patent is extended or adjusted under 35 U.S.C. 154(b) by 78 days.

(21) Appl. No.: 10/471,823

(22) PCT Filed: Mar. 1, 2002

(86) PCT No.: PCT/JP02/01906

§ 371 (c)(1),
(2), (4) Date: Sep. 15, 2003

(87) PCT Pub. No.: WO02/075315

PCT Pub. Date: Sep. 26, 2002

(65) Prior Publication Data

US 2004/0110246 A1 Jun. 10, 2004

(30) Foreign Application Priority Data

Mar. 15, 2001 (JP) .............................. 2001-073332

(51) Int. Cl.
*C12Q 1/32* (2006.01)
(52) U.S. Cl. ..................................................... 435/26
(58) Field of Classification Search ................ 435/26, 435/25, 14, 4
See application file for complete search history.

(56) References Cited

U.S. PATENT DOCUMENTS

| 4,683,198 A | 7/1987 | Ishikawa et al. |
| 6,541,215 B1 * | 4/2003 | Ebinuma et al. ............. 435/25 |

FOREIGN PATENT DOCUMENTS

| EP | 4-278098 | 2/1992 |
| EP | 1 099 765 A1 | 5/2001 |
| EP | 2002-148267 | 5/2002 |
| JP | 363248397 A * | 10/1988 |
| JP | 2000-298131 | 10/2000 |
| JP | 2001-197900 | 7/2001 |
| WO | 90/10711 | 9/1990 |
| WO | 91/12335 | 8/1991 |
| WO | WO 92/07953 | 5/1992 |
| WO | 96/01996 | 1/1996 |

OTHER PUBLICATIONS

Pitkanen et al, Eur. J. Clin. Chem. Clin. Biochem., V.35(10), pp. 761-776, (Oct. 1997(Abstract Only).*
Etchinson et al; Clinical Chemistry, vol. 43(3); pp. 533-539, (1997).*
Avigad et al; J. Biological Chemistry; vol. 243 (8); pp. 1936-1941, (1968).*
Pitkanen et al; Eur. J. Clin. Chem. Biochem.; vol. 35(10); pp. 761-766; (Oct. 1997).*
E. Pitkaenen European Journal of Clinical Chemistry and Clinical Biochemistry, vol. 35, No. 10, pp. 761-766 1997.
E. Pitkaenen Clinica Chimica ACTA, vol. 251, No. 1, pp. 91-103 1996.
E. Pitkänen European Journal of Clinical Chemistry and Clinical Biochemistry, vol. 35, No. 10, pp. 761-766 1997.
E. Pitkänen Clinica Chimica ACTA, vol. 251, No. 1, pp. 91-103 1996.
S. Akazawa, et al., Journal of Clinical Endocrinology and Metabolism, vol. 62, No. 5, 1 page, "Relationships Between Glucose and Mannose During Late Gestation in Normal Pregnancy and Pregnancy Complicated by Diabetes Mellitus: Concurrent Concentrations in Maternal Plasma and Amniotic Fluid", May 1986 (English Abstract only).
E. Pitkanen, et al., European Journal of Clinical Chemistry and Clinical Biochemistry, vol. 35, No. 10, 1 page, "Enzymatic Determination of Unbound D-Mannose in Serum", 1997 (English Abstract only).

* cited by examiner

*Primary Examiner*—Christopher R. Tate
*Assistant Examiner*—Amanda P. Wood
(74) *Attorney, Agent, or Firm*—Oblon, Spivak, McClelland, Maier & Neustadt, P.C.

(57) ABSTRACT

The present invention provides a screening method by which a prediabetic state can be more accurately determined and many test samples can be treated without physical burden on patients, and a diagnostic reagent used for it. By measuring a D-mannose concentration, preferably a D-mannose concentration and a glucose concentration, in a body fluid collected from a subject, and comparing them with their respective standard values, a patient in a prediabetic state can be detected. Further, the measurement of the mannose concentration is conducted by allowing an enzyme having an oxidizing activity on mannose by dehydrogenation to react on the mannose in a sample in the presence of an electron acceptor, and quantitatively determining the formed reductant of the electron acceptor.

18 Claims, 1 Drawing Sheet

METHOD OF SCREENING METHODS PREDIABETIC STATE AND SCREENING REAGENT

TECHNICAL FIELD

The present invention relates to a screening method by which a prediabetic state due to impaired glucose tolerance can easily be detected, and a screening reagent.

BACKGROUND ART

In Japan, it is now estimated that the number of diabetic patients is about 6.9 million, and by including the persons of impaired glucose tolerance which can be called a prediabetic state, it reaches 13.7 million. Further, it is said that in one in ten of the national population older than the age of 40 are diabetic patients.

Diabetes is known to develop via impaired glucose tolerance which used to be called a borderline type. Accordingly, the progress towards diabetes can be inhibited by detecting this state as early as possible and treating the patient.

Conventional clinical diagnosis of impaired glucose tolerance and diabetes, is made by measuring a fasting blood sugar level and measuring the blood sugar level 1 hour and/or 2 hours after a 75 g oral glucose tolerance test. The fasting blood sugar level (hereinafter referred to as "FBS") is used for screening because of its low load. According to the diagnostic criteria of Japan Diabetes Society, a level of less than 110 mg/dl is judged a normal type, 110 to 125 mg/dl, a borderline type, and 126 mg/dl or higher, a diabetic type. As the result of the above diagnosis, in a suspected case of diabetes, another 75 g oral glucose tolerance test is further conducted to make the final determination (with the blood sugar levels 2 hours after the glucose tolerance test, a level of less than 140 mg/dl is judged a normal type, 140 to 199 mg/dl, a borderline type, and 200 mg/ml or higher, a diabetic type).

However, the above determination method by means of FBS is not necessarily referred to as an accurate determination method because of the factors such as unstable type diabetes or contents of meal in the evening before the test. Further, the 75 g oral glucose tolerance test requires at least 2 hours and frequent blood sampling, and gives physical burden on patients, consequently that is not so favorable.

For detecting the prediabetic state or diabetic state, the following methods have been proposed for example.

(1) A method for detecting a prediabetic state by comparing the amount or increasing ratio of D-chiro-inositol in urine of mammal patients and that of healthy persons quantitatively determined in the same manner after a predetermined time, followed by the administration of sugar has passed (JP-A-2000-298131).

(2) A screening method for screening a mammal patient for the possibility of being diabetic using a urine sample from the patient, which comprises the steps of:1) keeping this sample in a bacteria-free environment, and 2) analyzing this sample about the presence of D-chiro-inositol; involving a step to define the absence of D-chiro-inositol, or the remarkably low level of D-chiro-inositol indicating no effect in vivo, as a state of being diabetic of the subject, wherein this low level is at least 3 orders lower than the level of non-diabetics (Japanese Patent No. 2,834,321).

(3) A method for detecting an insulin resistance in relation to the symptom of diabetes, wherein a chiro-inositol concentration as an index of the insulin resistance in relation to the symptom of diabetes in a urine sample or blood serum sample from mammal patients is measured (Japanese Patent No. 3,118,458).

(4) A method for screening a human for insulin resistance which comprises a step of measuring a concentration of D-chiro-inositol in body fluid, a step of measuring a concentration of myoinositol in body fluid, a step of calculating the ratio of myoinositol to D-chiro-inositol, and a step of comparing the ratio thus calculated with a ratio characteristic to the insulin resistance, wherein when the calculated ratio exceeds the ratio characteristic to the insulin resistance, this human is determined seemingly insulin resistive (Japanese International Publication No. 10-507826).

The above screening methods (1) to (4) are the methods for inspection which use urine and consequently require no blood sampling or the like, while urine sampling is needed within a predetermined time of period after glucose tolerance; for which the subject is placed under restraint for a predetermined time. From the above, these methods are inappropriate for general inspection. Further, they have a problem of being so complicated that it is impossible to treat a lot of test specimens.

DISCLOSURE OF INVENTION

Accordingly, it is an object of the present invention to provide a screening method and a screening reagent, by which the prediabetic state caused by impaired glucose tolerance can be more accurately determined without heavy burden on the subject in view of physical condition, time and costs, enabling the treatment of a lot of test specimens.

In order to accomplish the above object, one of the screening methods for a prediabetic state of the present invention comprises measuring a D-mannose concentration in a body fluid collected from a subject and comparing the D-mannose concentration with a predetermined standard value of D-mannose concentration.

Another screening method for prediabetic state of the present invention comprises measuring a D-mannose concentration and a glucose concentration in a body fluid collected from a subject; comparing the D-mannose concentration with a predetermined standard value of D-mannose concentration; and comparing the glucose concentration with a standard value of D-glucose predetermined concentration.

In the screening method of the present invention, the body fluid is preferably blood, blood plasma or blood serum of a subject under fasting condition. Further., the standard value of the D-mannose concentration is preferably an upper limit obtained by statistically treating the D-mannose concentration obtained by measuring blood, blood plasma or blood serum collected from a healthy person under fasting condition.

According to the screening method of the present invention, it is possible to more accurately detect unstable type diabetic patients, who are likely to be overlooked by a conventional judging method with FBS, and patients of prediabetic state such as potential impaired glucose tolerance showing normal FBS value.

On the other hand, the screening reagent for a prediabetic state of the present invention comprises an enzyme with an oxidizing activity on mannose by dehydrogenation in the presence of an electron acceptor and the electron acceptor, useful for the enzyme.

The screening reagent of the present invention preferably further comprises a glucose eliminator. Further, the enzyme is preferably a glucose dehydrogenase which is classified in EC 1.1.1.119, and more preferably, an aldohexose dehydrogenase derived from microorganisms which belong to *Gluconobacter* genus. Further, the glucose eliminator shall preferably contain glucose 6-position phosphorylating enzyme and adenosine triphosphate. Moreover, the electron acceptor is preferably a coenzyme NADP.

The screening reagent of the present invention enables to determine D-mannose quantitively and treat a lot of test specimens, because it uses an enzyme which directly reacts to D-mannose not through a complicated enzyme coupling system and has an oxidizing activity by dehydrogenation. Further, since the screening reagent of the present invention is hardly influenced by glucose in a sample, using the glucose eliminator enables the quantitative determination of D-mannose with more accuracy.

BEST MODE FOR CARRYING OUT THE INVENTION

Figure 1:
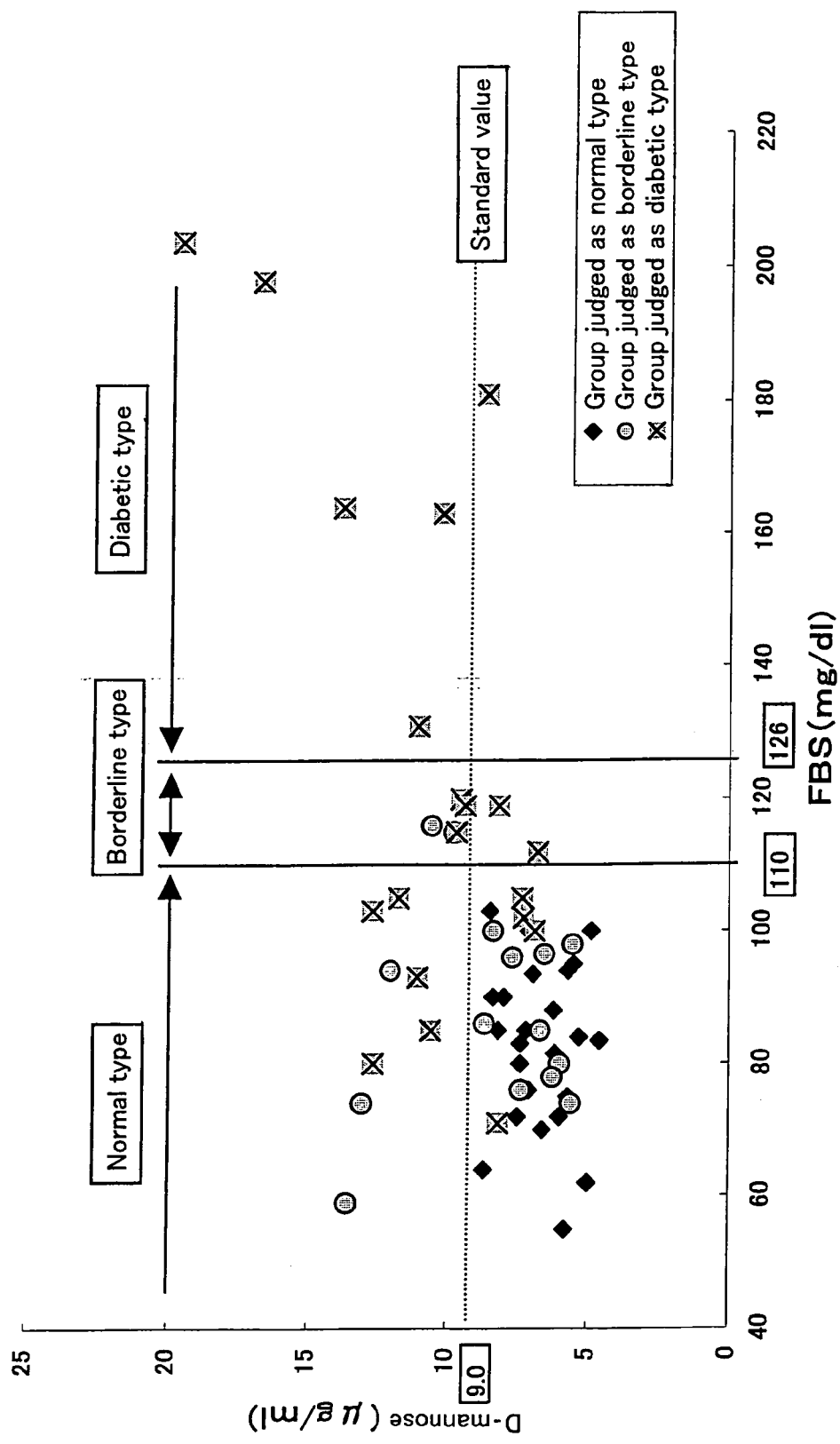
FIG. 1 is a graph showing results of comparison of a D-mannose concentration and a glucose concentration in blood plasma before glucose tolerance, by the screening method for prediabetic state of the present invention.

The prediabetic state detected by the screening method of the present invention is a state or condition that when sugar flows into blood by taking a meal, the sugar in blood cannot be sufficiently taken into peripheral tissues such as skeletal muscle, liver and adipose tissue, leading to an increase of blood sugar level, namely, impaired glucose tolerance. Here, the subject to whom the present invention is applied is mainly a human being, but can include mammals such as livestock and pets. In the present invention, "subject" includes such mammals.

In the method of the present invention for screening the subjects for prediabetic state, a D-mannose concentration in a body fluid collected from a subject is measured, and this concentration is compared with a predetermined standard value. Further, when the screening is more accurately conducted, measurement of a D-mannose concentration and measurement of a glucose concentration are conducted, and these concentrations are compared with the predetermined standard values, respectively.

As the above body fluid, urine, blood or the like collected from a subject may be mentioned. Particularly, the body fluid is preferably blood, blood plasma or blood serum, since the blood glucose level may also be measured when using them, and more preferably the one collected under fasting condition.

The standard value of the D-mannose concentration for judging the prediabetic state based on the D-mannose concentration measured from the body fluid of the subject, may be stated as follows. First, the D-mannose concentration in the body fluid (preferably, blood, blood plasma or blood serum) is measured of healthy persons in plural number (preferably, a few tens to a few hundreds) who have been preliminarily judged to be neither prediabetic nor diabetic in accordance with a diabetic diagnostic criteria; second, a normal range is determined from the results thereof by static treatment; and then take an upper limit of this normal range, or the like.

This standard value can be determined more accurately by conducting a preliminary test to many subjects. Accordingly, in the present invention, it is estimated from the below-mentioned examples that the standard value of a D-mannose concentration in blood is, although not particularly limited, about 9 µg/ml. Thus, in the below-mentioned examples, the D-mannose concentration of less than 9 µg/ml in blood is judged to be normal, and 9 µg/ml or higher is judged to be a suspected case of prediabetic state.

As a method for measuring the D-mannose concentration, conventional methods may be used. Among them, preferred is a method capable of treating many subjects, and particularly preferred is to use the below-mentioned screening reagent.

Further, as the standard value of a glucose concentration, the Diagnostic Criteria of Diabetes Mellitus of the Japan Diabetes Society (a level of less than 110 mg/dl is judged a normal type, 110 to 125 mg/dl, a borderline type, and 126 mg/dl or higher, a diabetic type) which has been used as the FBS standard, is preferably used. The glucose concentration can be measured by using a commercially available reagent for an automatic analyzer, or the like.

Hereinafter, the screening method for a prediabetic state of the present invention will be explained with reference to preferred embodiments.

First, the blood of a subject preferably in a fasting condition is collected in accordance with a conventional manner, from which preferably blood plasma or blood serum (hereinafter referred to simply as a sample) is subsequently separated. Here, the subject means all the persons who is inspected for a prediabetic state, including healthy persons, suspected diabetics, and diabetic patients.

Then, in the presence of an electron acceptor such as a coenzyme NADP, by having an enzyme with an oxidizing activity on mannose by dehydrogenation such as aldohexose dehydrogenase act on this sample, the formed reductant of the electron acceptor is quantitatively determined to measure the D-mannose concentration. Further, by using a commercially available analytical reagent, the glucose concentration of the same sample is also measured.

Thus measured D-mannose concentration and glucose concentration in blood are compared with each standard value to judge whether the subject is in the prediabetic state. As a specific judgment of the results, for example, a subject with the D-mannose concentration exceeding the standard value and glucose concentration within the normal range of the diagnostic criteria is suspected to have impaired glucose tolerance. Accordingly, re-inspection by 75 g oral glucose tolerance test should be recommended to such a subject.

Further, with respect to a subject with the glucose concentration exceeding the standard value, the possibility of impaired glucose tolerance is high, but even in this case, if the D-mannose concentration does not exceed the standard value, transient blood glucose increase may be suspected. In such a case, after asking the subject about the ingestion of meals or the like for confirmation, the possibility of transient impaired glucose tolerance is judged.

As mentioned above, by measuring the D-mannose concentration in blood under fasting condition, a person with potential impaired glucose tolerance who is hardly detected when judged only with FBS, can be easily detected. Further, the D-mannose concentration in blood show small fluctuation as compared with the fluctuation in blood glucose level caused by taking a meal and the like. Accordingly, with respect to the subject who is suspected of transient blood glucose increase, it is possible to judge whether or not the blood glucose increase is transient from the D-mannose concentration.

Further, by measuring the D-mannose concentration and glucose concentration in blood under fasting condition and comparing each of them with their standard values separately, it becomes possible to detect the subjects having impaired glucose tolerance or diabetes and having been detected so only by the 75 g oral glucose tolerance test (whose blood glucose level measured 2 hours after the glucose tolerance test is 140 mg/dl or higher).

Next, a reagent to be used for the above screening method for a prediabetic state will be explained.

Enzymes used in the present invention are not particularly limited so long as they have oxidizing activities on mannose by dehydrogenation in the presence of an electron acceptor. However, preferred is an enzyme classified in EC.1.1.1.119. Specifically, for example, a NADP dependent glucose dehydrogenase available from Acetobacter suboxydans as described in OKAMOTO's document (J.Biochem. 53(5), 1963, pp348–353), a NADP dependent aldohexose dehydrogenase available from *Gluconobacter* cerinus as described in AVIGAD et al.'s document (J. Biol. Chem. 243(8), 1968, pp1936–1941), a NAD dependent Aldohexose dehydrogenase as described in DAHMS et al.'s document (J. Biol. Chem. 247(7), 1972, pp2222–2227), etc., may be mentioned.

In the present invention, the above enzyme is particularly preferably aldohexose dehydrogenase derived from microorganisms belonging to *Gluconobacter* genus. As the microorganisms belonging to *Gluconobacter* genus, for example, *Gluconobacter* asaii (G.asaii) IFO 3276, *Gluconobacter* cerinus (G.cerinus) IFO 3267, *Gluconobacter* frateurii (G.frateurii) IFO 3264, *Gluconobacter* oxidans (G.oxydans) IFO 14819 and the like may be mentioned. In order to obtain the enzyme, first, the broken solution shall be prepared by culturing those microorganisms to collect the cells therefrom, and breaking them with ultrasonic treatment or the like; and then, the obtained broken solution is purified using any one, or a combination if required, of the following techniques, such as ammonium sulfate fractionation, column chromatographies including ion exchange chromatography, hydrophobic chromatograpy, hydroxyapatite gel, gel permeation, etc.

The concentration of the mannose dehydrogenase used, is not particularly limited, but it is preferably within the range of 0.1 to 100 units (u)/ml, more preferably 1 to 10 units (u)/ml. Here, one unit (u) of the enzyme mentioned above is defined as the amount of the enzyme required to form 1 μmol of NADPH per minute as measured by the following method.

Namely, 0.3 ml of 10 mM NADP, 0.85 ml of purified water and 0.3 ml of 500 rhM D-mannose are mixed with 1.5 ml of 200 mM Tris-HCl (pH9.0), and preincubated at 37° C. for 5 minutes; and then 0.05 ml of a sample is mixed with this preincubated solution, which started its reaction at 37° C., to determine the increase of absorbance at 340 nm per minute. As the blank, purified water was used instead of D-mannose. The titer was determined by the following formula by assigning each absorbance from the sample and the blank determined by the above measurement methods.

$$u/ml = ((\Delta OD \text{ sample/min} - \Delta OD \text{ blank/min}) \times 3/(6.3 \times 0.05)) \times \text{dilution ratio} \quad \text{Formula 1}$$

In the present invention, as the electron acceptor, one or two or more of coenzymes such as NAD and NADP, oxygen, phenazine methosulfate, dichlorophenol indophenol, ferricyanide, etc. may optionally be selected for use. Particularly preferred is a coenzyme NADP. The concentration of the electron acceptor used, is preferably within the range of 0.1 to 10 mmol/l, more preferably 0.5 to 2 mmol/l.

Further, in order to quantitatively determine the reductant of the electron acceptor, a coloring agent which develops a color by reducing the electron acceptor may be used in combination. Such coloring agent may optionally be selected depending upon the electron acceptor used. For example, in order to quantitatively determine NADPH as a reductant of the coenzyme NADP, a calorimetric method in which phenazine methosulfate or diaphorase as the electron carrier and tetrazolium salt are allowed to coexist therewith, and to which the formed formazan dye is subjected.

Further, since the mannose dehydrogenase used in the present invention also reacts with glucose other than mannose, particularly when the mannose in a biological sample such as blood serum or blood plasma is measured, the result is not a little influenced by glucose. Accordingly, in order to increase the measurement precision to the biological sample, it is preferred to use a glucose eliminator in combination. As the glucose eliminator, it is preferred to use one containing glucose 6-position phosphorylating enzyme and ATP.

As the glucose 6-position phosphorylating enzyme, glucokinase, hexokinase, etc. may be mentioned, and commercially available ones may be used without particular limitation so long as these belong to EC 2.7.1.2 or EC 2.7.1.1. More preferably, glucokinase which shows a high specificity to glucose is used. The amount thereof depends on the glucose amount in a sample, but usually 0.1 to 50 u/ml. Further, the ATP amount required for phosphorylation of glucose, which depends on the glucose amount in the sample, is usually 1 to mM. Furthermore, for accelerating the phosphorylation of glucose, usually, magnesium ions as inorganic or organic salts shall be contained in an amount of about 5 to 50 mM. The phosphorylation of glucose for glucose elimination is conducted in a buffer solution of pH 6 to 10, at 20 to 50° C., preferably to 37° C., for about 10 minutes immediately after the addition.

Further, as a method for eliminating glucose, for example, a conventional method using glucose oxidase and catalase may be used.

As a buffer solution used in the present invention, usual ones of pH 6 to 10 such as a phosphate buffer solution, glycine buffer solution, tris-HCl buffer solution, Good's buffer solution, boric acid buffer solution, etc., may be used.

As the screening reagent for a prediabetic state used in the present invention, a glucose eliminator and an enzyme for quantitative determination may be separately combined. More specifically, the reagent is preferably constituted by two reagents i.e. a first reagent containing an electron acceptor and a glucose eliminator, and a second reagent containing a mannose dehydrogenase.

After the reagent for quantitatively determining mannose is added to a sample and reaction is carried out, the measurement of the electron acceptor reduced in the reaction solution is conducted by, for example, measuring the absorbance at the absorption wavelength specific to the reductant of the electron acceptor, or measuring the intensity of color development of a coloring agent developed by the reductant of the electron acceptor.

Hereinafter, the present invention will be described specifically with reference to examples. However, it should be mentioned that the present invention is by no means restricted to these examples.

Preparation Example of Enzyme (Preparation of aldohexose dehydrogenase derived from *Gluconobacter* asaii)

*Gluconobacter* asaii (Deposition No. IFO 3276, Deposition Authority: Foundation, Institute for Fermentation, 17–85, Juso-honmachi 2-chome, Yodogawa-ku, Osaka-shi, Osaka, Japan) was inoculated on a medium containing 0.5% of yeast extract and 1% of fructose, and shake cultured at 28° C. for 24 hours, followed by centrifugation to obtain cells.

The cells were suspended in a 20 mM phosphate buffer solution (pH 7), treated with an ultrasonic oscillator under ice-cooling. And then, a crude enzyme solution was obtained by removing the cell residues from the broken solution after centrifugal separation.

Ammonium sulfate powder was added to this crude enzyme solution and dissolved therein so that the ammonium sulfate would be 30% of saturation, and the precipitated protein was removed by centrifugal separation. The obtained supernatant was loaded on to a Butyl Toyopearl column to adsorb the enzyme, and the enzyme was eluted with a 20 mM phosphate buffer solution (pH 7) containing ammonium sulfate in such an amount of 30 to 0% of saturation.

The enzymatic activity of each eluted fraction was measured and the active fraction was collected, and the active fraction was desalted by dialysis with a 20 mM phosphate buffer solution (pH 7). Then, this was loaded on to a DEAE Toyopearl column to adsorb the enzyme, and the enzyme was eluted with a 20 mM phosphate buffer solution (pH 7) containing 0 to 0.25M NaCl.

The enzymatic activity of each eluted fraction was measured and the active fraction was collected, and the active fraction was desalted by dialysis with a 20 mM phosphate buffer solution (pH 7). Then, this was loaded on to a Hydroxyapatite column to adsorb the enzyme, and the enzyme was eluted with a 20 to 150 mM phosphate buffer solution (pH 7). The enzymatic activity of each eluted fraction was measured and the active fraction was recovered, and this was used as a purified enzyme solution.

EXAMPLE 75 g glucose oral glucose tolerance test was conducted on 59 persons as suspected subjects of diabetes, and blood sampling was conducted immediately before sugar tolerance (fasting state), or at the time of 30 minutes, 60 minutes and 120 minutes, respectively, after the sugar tolerance, using a blood sampling tube for blood sugar measurement. Then, the blood plasma was separated, and the glucose concentration in each blood plasma was measured with a commercially available reagent for an automatic analyzer, "Pureauto S-GLU" (trade name, manufactured by Daiichi Pure Chemicals Co., Ltd.).

On the other hand, the measurement of D-mannose concentration was conducted by using a reagent for quantitative determination comprising the first reagent and the second reagent as mentioned below. Namely, 256 µl of the first reagent was added to 8 µl of each blood plasma, and reacted at 37° C. for 5 minutes, and then 56 µl of the second reagent was added and likewise reacted at 37° C. for 5 minutes. Then, absorbance was measured by two-point assay with two wavelengths of a main wavelength of 450 nm and a sub wavelength of 700 nm. These operations were carried out by Hitachi 7150 Model Automatic Analyzer. As a standard substance, a commercially available D-mannose was used in the form of an aqueous solution. Further, with respect to a sample which may possibly cause measurement errors in this measurement system by e.g. hemolysis, a blank reagent was separately prepared without aldohexose dehydrogenase from the second reagent, and respective samples were measured at the same time, and then the obtained non-specific color development was subtracted from specific color development to correct the measurement errors.

First Reagent:
   125 mM Tris-HCl buffer solution
   1.25 mM NADP
   0.75 mM WST-1
   1.25% Tween 20
   6.25 u/ml Diaphorase
   12.5 u/ml Glucokinase
   10 mM ATP
   2 mM Magnesium acetate
   (pH 8.5)

Second Reagent:
   20 mM Phosphate buffer solution
   0.23 u/ml Aldohexose dehydrogenase (the enzyme obtained in the above preparation example)
   (pH 7.0)

The measurement results are indicated in FIG. 1.

Namely, from the results of 75 g oral glucose tolerance test, the subjects were judged three groups as a normal type, a borderline type and a diabetic type in accordance with the diagnostic criteria of Japan Diabetes Society. As a result, the subjects were judged 24 persons as a normal type, 15 persons as a borderline type, and 20 persons as a diabetic type. In FIG. 1, the persons judged to be a normal type are indicated by ♦, the persons judged to be a borderline type are indicated by ○, the persons judged to be a diabetic type are indicated by x.

On the other hand, in FIG. 1, the ordinate axis represents a D-mannose concentration, and the abscissa axis represents a glucose concentration in blood plasma immediately before the glucose tolerance (blood sugar level under fasting condition: FBS), and respective subjects were plotted out.

In FBS, a level of less than 110 mg/dl was classified into a normal type, a level of 110 to 125 mg/dl was classified into a borderline type, and a level of 126 mg/dl or higher was classified into a diabetic type. By classification with FBS only, the normal type was 46 persons, the borderline type was 7 persons, and the diabetic type was 6 persons.

Further, the standard value of the D-mannose concentration in this example was calculated by a statistical manner from the D-mannose concentration of 24 persons judged to be a normal type in accordance with the diagnostic criteria of Japan Diabetes Society. Specifically, assuming that the D-mannose concentration of 24 persons judged to be a normal type shows a normal distribution, and estimating that the normal value range of healthy persons is "an average value ±2×a standard deviation", the normal value range of healthy persons is 6.6±2.4 µg/ml, and the upper limit is calculated to be 9 µg/ml. Further, the 95% confidence interval of this upper limit is calculated to be 7.3 to 10.7 µg/ml. However, in this example, the standard value was set to be 9 µg/ml, the upper limit.

As a result, it is found that 10 of 13 subjects who exceeded 110 mg/dl as the standard value of FBS and were thereby judged to be the borderline type or diabetic type based on the results of the oral glucose tolerance test, exceed the standard value of the D-mannose concentration in blood plasma. Namely, it is found that 70 to 80% of subjects of the borderline type or diabetic type who can be detected by FBS, can be detected also by the measurement of the D-mannose concentration.

Further, the 46 persons who were judged to be a normal type in the result of FBS, included 22 subjects who are classified to be a borderline type or a diabetic type i.e. suspected to be a impaired glucose tolerance, in the result of the oral glucose tolerance test. Although these subjects are in a borderline type state or a diabetic type state, they were classified to be a normal type and overlooked in the conventional diagnosis system using only FBS in the primary test. However, according to the present invention using a D-mannose concentration in blood plasma, it is found that 8 of the above 22 subjects exceeded the standard value.

On the other hand, with the 24 subjects who are classified to be a normal type in both FBS and the oral glucose tolerance test (♦ in FIG. 1), no one was confirmed to exceed the standard value of the D-mannose concentration in blood plasma.

From these results, by measuring the D-mannose concentration in blood plasma, it was found possible to detect or find out with high probability the borderline type subjects with light impaired glucose tolerance, namely who are in the prediabetic state, who have been heretofore overlooked because of the normal FBS values of themselves.

INDUSTRIAL APPLICABILITY

As mentioned above, the present invention provides a screening method for a prediabetic state by which it is possible to more accurately find unstable diabetic patients and prediabetic patients in light impaired glucose tolerance, which have been readily overlooked by conventional determination methods by use of blood glucose value in a fasting condition. As the result, it becomes possible to find in an early stage the prediabetic subjects in light impaired glucose tolerance and the like, appropriately treat at an early stage with a medicine or the like to prevent the progress toward diabetes, and further monitor the treatment process.

Further, by incorporating the screening method of the present invention into the inspection of diabetes presently used, the present invention can be applied to the construction of the total diabetes diagnosis system, for example, making a panel of inspection items, and development of software for this purpose, etc.

Further, since the screening reagent for a prediabetic state of the present invention has a simple reaction system, it can easily be applicable to various automatic analyzers and is suitable for treatment of many test samples.

The invention claimed is:

1. A method for detecting a subject in a prediabetic state comprising:
   measuring the D-mannose concentration in a body fluid collected from a subject at risk of or suspected of developing diabetes and
   comparing the D-mannose concentration with a predetermined standard value of D-mannose concentration in normal subjects; and
   measuring the glucose concentration in a body fluid collected from said subject, and
   comparing the glucose concentration with an FBS (fasting blood sugar) standard;
   wherein an elevated concentration of D-mannose compared to the predetermined standard value of D-mannose and a glucose concentration within a normal range concentration is indicative of a prediabetic state;
   wherein measuring the D-mannose concentration comprises:
   contacting said sample with an enzyme having oxidizing activity on mannose in the presence of an electron acceptor, and
   measuring the amount of reductant formed as an indication of mannose concentration.

2. The method of claim 1, wherein the enzyme having oxidizing activity on mannose is aldohexose dehydrogenase.

3. The method of claim 1, wherein the enzyme having oxidizing activity on mannose is classified as EC 1.1.1.119.

4. The method of claim 1, wherein the enzyme having oxidizing activity on mannose is an NADP dependent glucose dehydrogenase, an NADP dependent aldohexose dehydrogenase, or an NAD dependent aldohexose dehydrogenase.

5. The method of claim 1, wherein the enzyme having oxidizing activity on mannose is obtained from *Gluconobacter*.

6. The method of claim 1, wherein the electron acceptor is the coenzyme NADP.

7. The method of claim 1, wherein the electron acceptor is at least one of coenzyme NAD, oxygen, phenazine methosulfate, dichlorophenol, indophenol, or ferricyanide.

8. The method of claim 1, wherein the concentration of the electron acceptor ranges from 0.1 to 10 mmol/l.

9. The method of claim 1, further comprising adding a coloring agent which develops a color by reducing the electron acceptor.

10. The method of claim 1, wherein the mannose concentration is determined in the presence of a glucose eliminator.

11. The method of claim 1, wherein the mannose concentration is determined in the presence of a glucose eliminator, which comprises a glucose-6-position phosphorylating enzyme of EC 2.7.1.2 or EC 2.7.1.1, and adenosine triphosphate (ATP).

12. The method of claim 1, wherein the predetermined standard value of D-mannose concentration is 9μg/ml, and wherein a concentration of mannose above 9μg/ml is indicative of a prediabetic state.

13. The method of claim 1, wherein the standard value of the D-mannose concentration is the upper limit obtained by a statistical analysis of D-mannose concentration values obtained by measuring blood, blood plasma, or blood serum collected from a healthy individual under fasting conditions.

14. The method of claim 1, wherein the sample is blood, blood plasma or blood serum.

15. The method of claim 1, wherein the sample is blood, blood plasma or blood serum obtained from a fasting subject.

16. The method of claim 1, wherein the FBS (fasting blood sugar) standard is a normal type diagnostic criterion or a borderline type diagnostic criterion.

17. The method of claim 16, wherein a glucose concentration of less than 126 mg/dl is indicative of a prediabetic state.

18. A method for detecting a subject with impaired glucose tolerance comprising:
   measuring the D-mannose concentration in a body fluid collected from a subject at risk of or suspected of developing diabetes and
   comparing the D-mannose concentration with a predetermined standard value of D-mannose concentration in normal subjects; and
   measuring the glucose concentration in a body fluid collected from said subject, and
   comparing the glucose concentration with an FBS (fasting blood sugar) standard;
   wherein an elevated concentration of D-mannose compared to the predetermined standard value of D-mannose and an elevated glucose concentration is indicative of impaired glucose tolerance;
   wherein measuring the D-mannose concentration comprises:
   contacting said sample with an enzyme having oxidizing activity on mannose in the presence of an electron acceptor, and
   measuring the amount of reductant formed as an indication of mannose concentration.

* * * * *

UNITED STATES PATENT AND TRADEMARK OFFICE
CERTIFICATE OF CORRECTION

| | |
|---|---|
| PATENT NO. | : 7,198,905 B2 |
| APPLICATION NO. | : 10/471823 |
| DATED | : April 3, 2007 |
| INVENTOR(S) | : Ebinuma et al. |

It is certified that error appears in the above-identified patent and that said Letters Patent is hereby corrected as shown below:

On the title page, Item (54), the title in incorrect. Item (54) should read:
-- [54]  METHOD OF SCREENING PREDIABETIC
       STATE AND SCREENING REAGENT--

Signed and Sealed this

Twenty-ninth Day of May, 2007

JON W. DUDAS
*Director of the United States Patent and Trademark Office*